(12) United States Patent
Ideker et al.

(10) Patent No.: US 7,920,918 B2
(45) Date of Patent: Apr. 5, 2011

(54) APPARATUS AND METHOD FOR TREATING VENTRICULAR FIBRILLATION AND VENTRICULAR TACHYCARDIA

(75) Inventors: Raymond E. Ideker, Birmingham, AL (US); Derek J. Dosdall, Birmingham, AL (US); James P. Ruse, Clermont, FL (US); Greg Ruse, legal representative, Clermont, FL (US); Richard B. Ruse, Atlanta, GA (US); Scott J. Bohanan, Duluth, GA (US)

(73) Assignees: Ruse Technologies, LLC, Atlanta, GA (US); The UAB Research Foundation, Birmingham, AL (US)

( * ) Notice: Subject to any disclaimer, the term of this patent is extended or adjusted under 35 U.S.C. 154(b) by 275 days.

(21) Appl. No.: 12/272,296

(22) Filed: Nov. 17, 2008

(65) Prior Publication Data
US 2009/0157131 A1 Jun. 18, 2009

Related U.S. Application Data

(60) Provisional application No. 60/988,536, filed on Nov. 16, 2007.

(51) Int. Cl.
*A61N 1/00* (2006.01)
(52) U.S. Cl. .......................................................... 607/5
(58) Field of Classification Search .................. 607/4, 5, 607/14, 15, 119, 2, 7, 9
See application file for complete search history.

(56) References Cited

U.S. PATENT DOCUMENTS

| 7,389,140 B1 * | 6/2008 | Kroll | 607/9 |
| 2005/0131475 A1 * | 6/2005 | Smits | 607/14 |

* cited by examiner

*Primary Examiner* — George Manuel
*Assistant Examiner* — Robert N Wieland
(74) *Attorney, Agent, or Firm* — William H. Dippert; Eckert Seamans Cherin & Mellott, LLC

(57) ABSTRACT

An apparatus for treating ventricular fibrillation or ventricular tachycardia comprises means for dynamically steering or selecting two or more current vector paths sequentially or simultaneously for defibrillation so as to change the transmembrane potential in the left and right ventricles sufficiently to halt VF or VT.

28 Claims, 7 Drawing Sheets

SYSTEM DIAGRAM

SYSTEM DIAGRAM

AMPLIFIER ARRAY

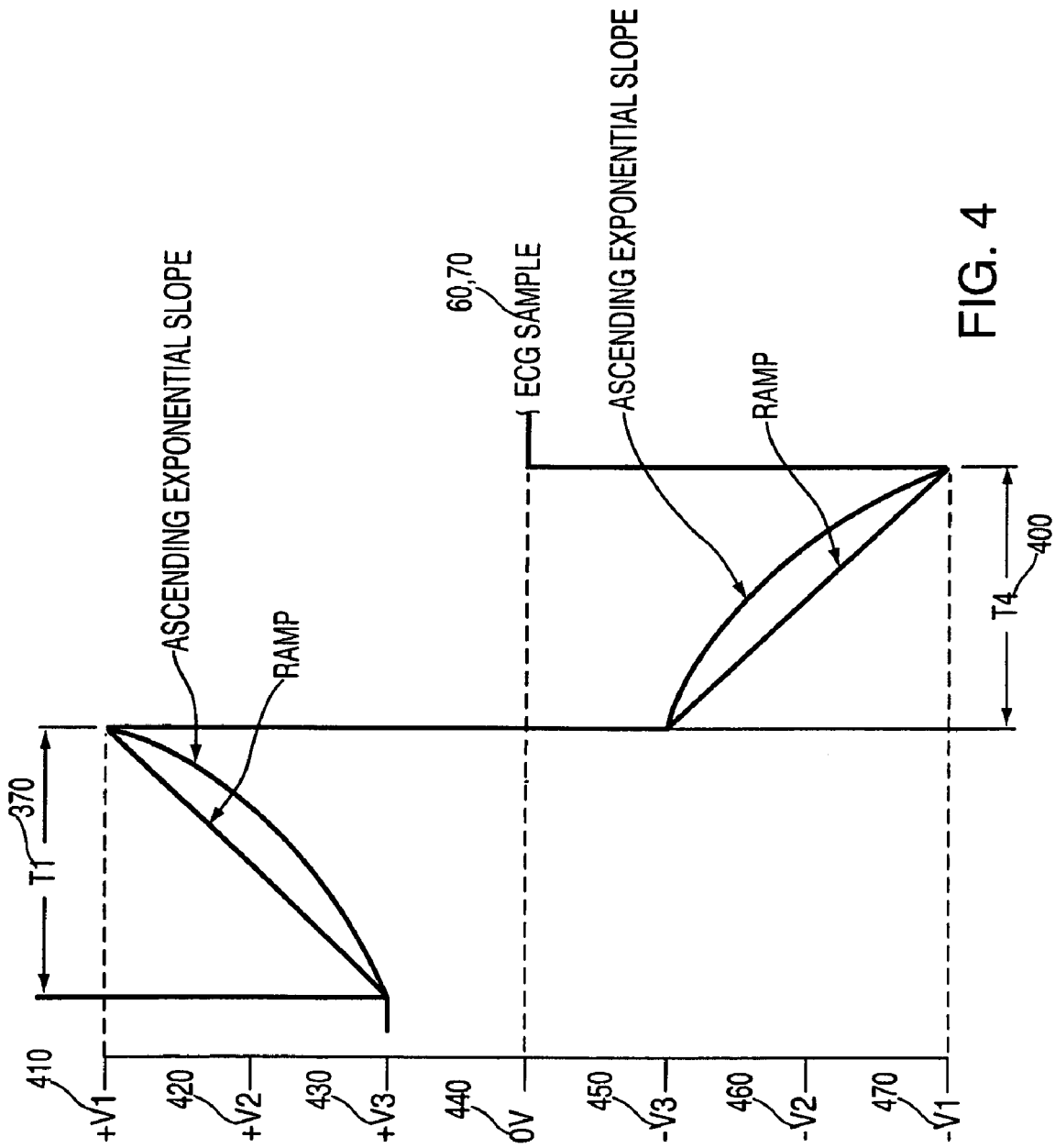

APPARATUS AND METHOD FOR TREATING VENTRICULAR FIBRILLATION AND VENTRICULAR TACHYCARDIA

CROSS-REFERENCE TO RELATED APPLICATION

This application is based upon and corresponds to commonly assigned, U.S. Provisional Patent Application Ser. No. 60/988,536, filed Nov. 16, 2007, incorporated herein by reference in its entirety.

FIELD OF THE INVENTION

This invention is directed to the electrical management of cardiac arrhythmias or abnormal heart rhythms that occur in the walls of the ventricular or lower chambers of the human heart. More particularly, the invention is directed to the treatment of ventricular fibrillation and ventricular tachycardia, which may cause sudden cardiac death due to a variety of causes.

BACKGROUND OF THE INVENTION

Ventricular fibrillation [VF] is a cause of cardiac arrest and sudden cardiac death (SCD). During VF, the ventricular muscle contracts in a much less organized pattern than during normal sinus rhythm, so the ventricles fail to pump blood into the arteries and systemic circulation. VF is a sudden lethal arrhythmia responsible for many deaths in the Western world, mostly brought on by ischemic heart disease. VF which occurs in approximately 2 out of 10,000 people per year is a medical emergency. If the arrhythmia continues for more than a few seconds, blood circulation will cease, as evidenced by lack of pulse, blood pressure and respiration, and death will occur.

Despite much work, the underlying nature of VF is not completely understood. Most episodes of VF occur in diseased hearts, but others occur in structurally normal hearts. Much work still has to be done to elucidate the mechanisms of VF.

Ventricular tachycardia [VT] is a tachyarrhythmia originating from an ectopic ventricular region, characterized by a rate typically greater than 100 beats per minute and wide QRS complexes. VT may be monomorphic, i.e., originating from a single repeating pathway with identical QRS complexes, or polymorphic, i.e., following changing pathways, with varying QRS complexes. Non-sustained VT is defined as an episode of tachycardia of less than 30 seconds duration; longer runs are considered sustained VT.

No absolute ECG criteria exist for establishing the presence of VT. However, several factors suggest VT, including the following; Rate greater than 100 beats per minute (usually 150-200), wide QRS complexes (>120 ms), presence of atrioventricular (AV) dissociation, and fusion beats, which are integrated into the VT complex.

VT may develop without hemodynamic deterioration. Nevertheless, it often causes severe hemodynamic compromise and may deteriorate rapidly into VF. Therefore, this tachyarrhythmia also must be addressed swiftly to avoid morbidity or mortality.

VT is defined as three or more beats of ventricular origin in succession at a rate greater than 100 beats per minute. There are no normal-looking QRS complexes. The rhythm is usually regular, but on occasion it may be modestly irregular. The arrhythmia may be either well-tolerated or associated with grave, life-threatening hemodynamic compromise. The hemodynamic consequences of VT depend largely on the presence or absence or myocardial dysfunction (such as might result from ischemia or infarction) and on the rate of VT. Atrioventricular dissociation usually is present, which means that the sinus node is depolarizing the atria in a normal manner at a rate either equal to, or slower than, the ventricular rate. Thus, sinus P waves sometimes can be recognized between QRS complexes. They bear no fixed relation to the QRS complexes unless the atrial and ventricular rates happen to be equal. Conduction from atria to ventricles is usually prevented because the AV node or ventricular conduction system is refractory due to ventricular depolarizations caused by the VT.

VT is uncommon in the absence of apparent heart disease. It can develop as an early or a late complication of a myocardial infarction, or ischemia, during the course of cardiomyopathy, valvular heart disease, or myocarditis, or following heart surgery.

Myocardial infarcts heal by forming scar tissue which can lead to VT. This can occur days, months, or years after the infarction. VT can also result from anti-arrhythmic medications (an undesired effect) or from altered blood chemistries (such as low potassium or magnesium levels), pH (acid-base) changes, or insufficient oxygenation.

A common mechanism for VT is reentry (re-stimulation of the electrical conductive pathway from a single initial stimulus). "Torsade de pointes" is a form of VT with a specific variation or irregularity in the conduction of the ventricular stimulus.

In recent years, a preferred treatment for many chronic (long-term) VTs consists of implanting a cardiac device, such as an implantable cardioverter defibrillator (ICD). The ICD is usually implanted in the chest, like a pacemaker, and it is connected to the heart with intracardiac wires.

The ICD is programmed by the implanting physician to sense VT when it is occurring to administer a DC shock to convert/abort it. The ICD may also be programmed to pace the ventricles at a rapid rate, anti-tachycardia pacing (ATP), to attempt to entrain and halt the reentry circuit maintaining the VT. If the ATP is unsuccessful, an electrical shock is then given by the ICD for conversion. The VT may also require the use of concomitant anti-arrhythmic agents to prevent repeated firing of the ICD. Most VF episodes are preceded by VT, so it is highly desirable to prevent or halt VT before the arrhythmia degrades into VF where the heart is severely compromised hemodynamically.

OBJECTS OF THE INVENTION

It is an object of the invention to provide a method and an ICD for dynamically steering or selecting two or more current vector paths sequentially or simultaneously for defibrillation or cardioversion.

It is likewise an object of the invention to provide a method and a high power version of the ICD circuitry that will be useful in external defibrillation as in devices such as Automatic Emergency Defibrillators [AED's] used in public places such as schools and airports.

It is also an object of the invention to provide an implantable ventricular defibrillation device which uses less energy than conventional defibrillation devices by utilizing sequential or simultaneous shocks at a reduced voltage amplitude, thereby reducing pain levels associated with electrical shocks.

It is a further object of the invention to provide an implantable defibrillator which defibrillates with lower peak voltage and current waveforms which minimize tissue stunning and damage.

It is yet a further object of the invention to defibrillate using biphasic sequential and simultaneous shocking pulses that are in the range of from about 2.5 ms to about 8 ms positive and negative time periods to minimize energy consumption.

The above and other objects of the present invention will become more readily apparent when reference is made to the following descriptions taken in conjunction with the attached detail drawings.

SUMMARY OF THE INVENTION

According to the invention, a method and an ICD are provided for dynamically steering or selecting two or more current vector paths sequentially or simultaneously for defibrillation or cardioversion. The purpose of the invention is to change the transmembrane potential in the left and right ventricles sufficiently to halt VF or VT with smaller shocks than required using traditional devices which defibrillate through a single current path or using devices that deliver shocks across two or more current pathways but that cannot dynamically alter the voltage and current amplitude through each pathway.

An aspect of the invention is directed to providing a method and a high power version of the ICD circuitry that will be useful in external defibrillation as in devices such as Automatic Emergency Defibrillators [AED's] used in public places such as schools and airports. Also, very high power laboratory devices can use the same circuit principles as the lower power implantable devices or ICDs for scientific studies in animals.

A method to deliver biphasic ascending or descending exponential, ramp, or damped sinusoidal waveforms which are most efficient with respect to the transmembrane potential response within the myocardium comprises using an amplifier array where any two, three, or four amplifiers and their respective electrodes may be driven differentially as to draw current through selected current pathways or different angular perspectives within the right and left ventricles to rapidly terminate VF and VT. Also, any one amplifier may be driven differentially to any of the other three amplifiers simultaneously using the same arbitrary waveform, or any one amplifier may be driven differentially to any of the other three amplifiers sequentially using individual arbitrary waveforms at different or equal voltage and current amplitudes. By use of this approach, many combinations of shock deliveries are possible and can be selected by the electrophysiologist based on individual patient requirements for cardioversion or defibrillation. The pre-programmed software protocols will be easily selected by an electrophysiologist.

The amplifiers will process any waveform and voltage amplitude through the ventricles and atria as directed and selected by an electrophysiologist such as ascending or descending exponential, ramp, damped sine, square, sine, triangle, saw tooth, etc. The voltage amplitude range shall be from about 0 to about 800 VDC.

In another aspect of the invention an implantable or external ventricular defibrillation device is provided which uses less energy than conventional defibrillation devices by utilizing sequential or simultaneous shocks at a reduced voltage amplitude, thereby reducing pain levels associated with electrical shocks.

In another aspect of the invention an implantable or external defibrillator is provided which defibrillates with lower peak voltage and current waveforms which minimize tissue stunning and damage.

In another aspect of the invention defibrillation occurs using biphasic sequential and simultaneous shocking pulses that are in the range of from about 2.5 ms to about 8 ms, optionally from about 3 ms to 6 ms, positive and negative time periods to minimize energy consumption.

According to an embodiment of the invention, a method of treating ventricular fibrillation or ventricular tachycardia comprises dynamically steering or selecting two or more current vector paths sequentially or simultaneously for defibrillation so as to change the transmembrane potential in the left and right ventricles sufficiently to halt VF or VT.

According to another embodiment of a method of the invention, the method is carried out with smaller shocks than required using traditional devices which defibrillate through a single current path or using devices that deliver shocks across two or more current pathways but that cannot dynamically alter the voltage and current amplitude through each pathway.

According to another embodiment of the invention, an ICD is used.

According to another embodiment of the invention, a method can treat VT of any mechanism, including but not limited to, automatic, triggered, or reentrant or VF, whether occurring in the structurally normal heart, hypertrophic heart, or myopathic heart (independent of origin of underlying structural heart disease).

According to another embodiment of the invention, a method of treating ventricular fibrillation or ventricular tachycardia comprises delivering biphasic ascending or descending exponential, ramp, or damped sinusoidal waveforms which are most efficient with respect to the transmembrane potential response within the myocardium by using an amplifier array where any two, three, or four amplifiers and their respective electrodes may be driven differentially as to draw current through selected current pathways or different angular perspectives within the right and left ventricles to rapidly terminate VF and VT.

According to another embodiment of a method or apparatus of the invention, any one amplifier may be driven differentially to any of the other three amplifiers simultaneously using the same arbitrary waveform or any one amplifier may be driven differentially to any of the other three amplifiers sequentially using individual and different arbitrary waveforms at different or equal voltage and current amplitudes.

According to another embodiment of a method of the invention, the method comprises "Hot Can" shocking or intracardiac electrode shocking as specified or programmed by an electrophysiologist.

According to another embodiment of a method of the invention, the electrophysiologist can select pre-programmed and pre-defined software waveform protocols, wherein many combinations of shock deliveries are possible based on individual patient requirements for cardioversion or defibrillation.

According to another embodiment of a method of the invention, the individual requirements are selected from the software protocol based on various medical criteria as defined by the electrophysiologist.

According to another embodiment of a method of the invention, the various medical criteria include, but are not limited to, gender, size, weight, age, and degree or type of heart disease.

According to another embodiment of a method or apparatus of the invention, waveform protocols are pre-programmed and pre-defined and are loaded into a microcontroller memory for quick execution.

According to another embodiment of a method or apparatus of the invention, 50 to 100 or more protocols can be stored in the microcontroller for an electrophysiologist to select from.

According to another embodiment of a method or apparatus of the invention, arbitrary waveforms can be delivered to multiple electrode configurations and multiple sequential or simultaneous shocking paths can be employed.

According to another embodiment of a method or apparatus of the invention, the amplifiers will process any waveform through the ventricles and or atria as directed by an electrophysiologist such as ascending or descending exponential, damped sine, ramp, square, sine, triangle, ramp, saw tooth, etc.

According to another embodiment of a method or apparatus of the invention, the voltage amplitude range will be in the range of from about 0 to about 800 VDC.

According to another embodiment of the invention, a method of treating ventricular fibrillation or ventricular tachycardia comprises providing an implantable or external ventricular defibrillation and or ventricular tachycardia cardioversion device which uses less energy than conventional defibrillation devices thereby reducing pain levels, tissue stunning, and damage associated with very high voltage electrical shocks.

According to another embodiment of a method or apparatus of the invention, transmembrane potentials are achieved using lower leading edge peak voltages and sequential or simultaneous arbitrary waveform shocks.

According to another embodiment of a method or apparatus of the invention, biphasic sequential or simultaneous shocking pulses are in the range of from about 2.5 ms to about 8 ms, optionally from about 3 ms to about 6 ms, positive and negative time periods, respectively, to minimize energy consumption and conserve battery life.

According to another embodiment of the invention, an apparatus for treating ventricular fibrillation or ventricular tachycardia comprises means for dynamically steering or selecting two or more current vector paths sequentially or simultaneously for defibrillation so as to change the transmembrane potential in the left and right ventricles sufficiently to halt VF or VT.

According to another embodiment of the invention, the apparatus accomplishes its purpose with smaller shocks than required using traditional devices which defibrillate through a single current path or using devices that deliver shocks across two or more current pathways but that cannot dynamically alter the voltage and current amplitude through each pathway.

According to another embodiment of the invention, the apparatus comprises an ICD or external defibrillator.

According to another embodiment of the invention, the apparatus can treat VT of any mechanism, including but not limited to, automatic, triggered, or reentrant or VF, whether occurring in the structurally normal heart, hypertrophic heart, or myopathic heart (independent of origin of underlying structural heart disease).

According to another embodiment of the invention, an apparatus for treating ventricular fibrillation or ventricular tachycardia comprises means for delivering a biphasic ascending exponential, ramp, or damped sinusoidal waveforms which are most efficient with respect to the transmembrane potential response within the myocardium by using an amplifier array where any two, three, or four amplifiers and their respective electrodes may be driven differentially as to draw current through selected current pathways or different angular perspectives within the right and left ventricles to rapidly terminate VF and VT.

According to another embodiment of an apparatus of the invention, any one amplifier may be driven differentially to any of the other three amplifiers simultaneously using the same arbitrary waveform or any one amplifier may be driven differentially to any of the other three amplifiers sequentially using individual arbitrary waveforms at different or equal voltage and current amplitudes.

BRIEF DESCRIPTION OF THE DRAWINGS

FIGS. 4 and 4A depict ascending or descending exponential, ramp, and damped sinusoidal waveforms with the time periods identified.

DETAILED DESCRIPTION OF THE DRAWINGS

Figure 1:
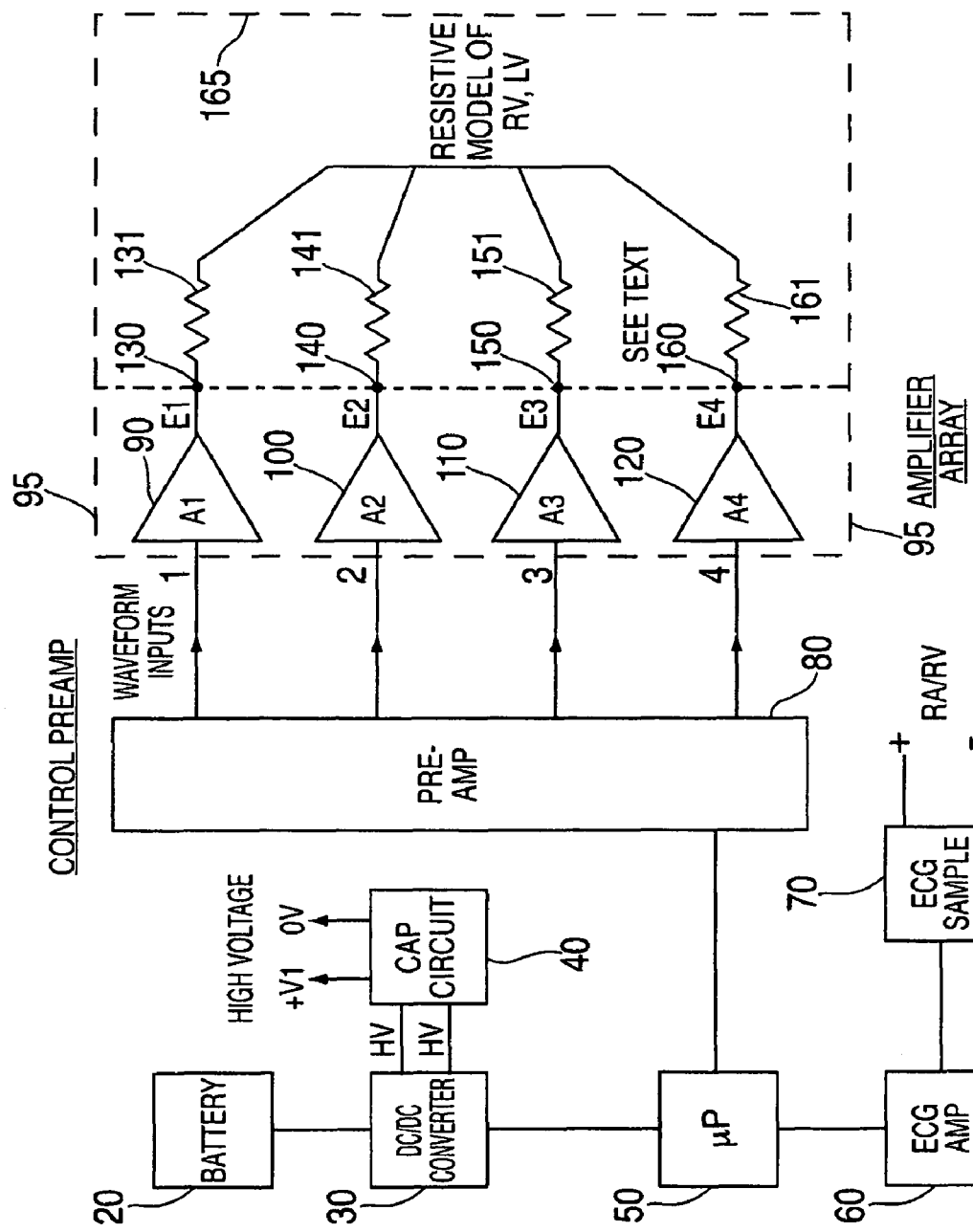
FIG. 1 depicts a system overview of an implantable ventricular defibrillation device and its major components and circuit architecture.

FIG. 1 illustrates the defibrillation system according to the present invention. The battery 20 provides power to the pulse width modulated [PWM] and regulated DC/DC converter 30 which in turn distributes a control voltage to the microprocessor 50, the ECG Amp 60 and the ECG Sense Analyzer 70 as well as the control preamp 80. The DC/DC 30 converter also distributes high voltage to the capacitor circuit 40 and the four amplifiers 90, 100, 110, and 120. The PWM regulated DC/DC converter shall have a dynamic, programmable current limit circuit as part of the overall converter design. Electrodes E1, E2, E3 and E4 130, 140, 150, and 160 with their respective wires are installed electrodes that are placed chronically in the SVC, right atria, and right ventricle. These structures are entered from the SVC and then through the right atrium as specified by the electrophysiologist cardiologist. Also illustrated are heart muscle resistances 165 depicted by 131, 141, 151, and 161. These resistances represent the effective defibrillation load in which the voltage and current from the amplifiers deliver defibrillation shocks between any two, three, or four amplifiers sequentially or simultaneously.

Figure 2:
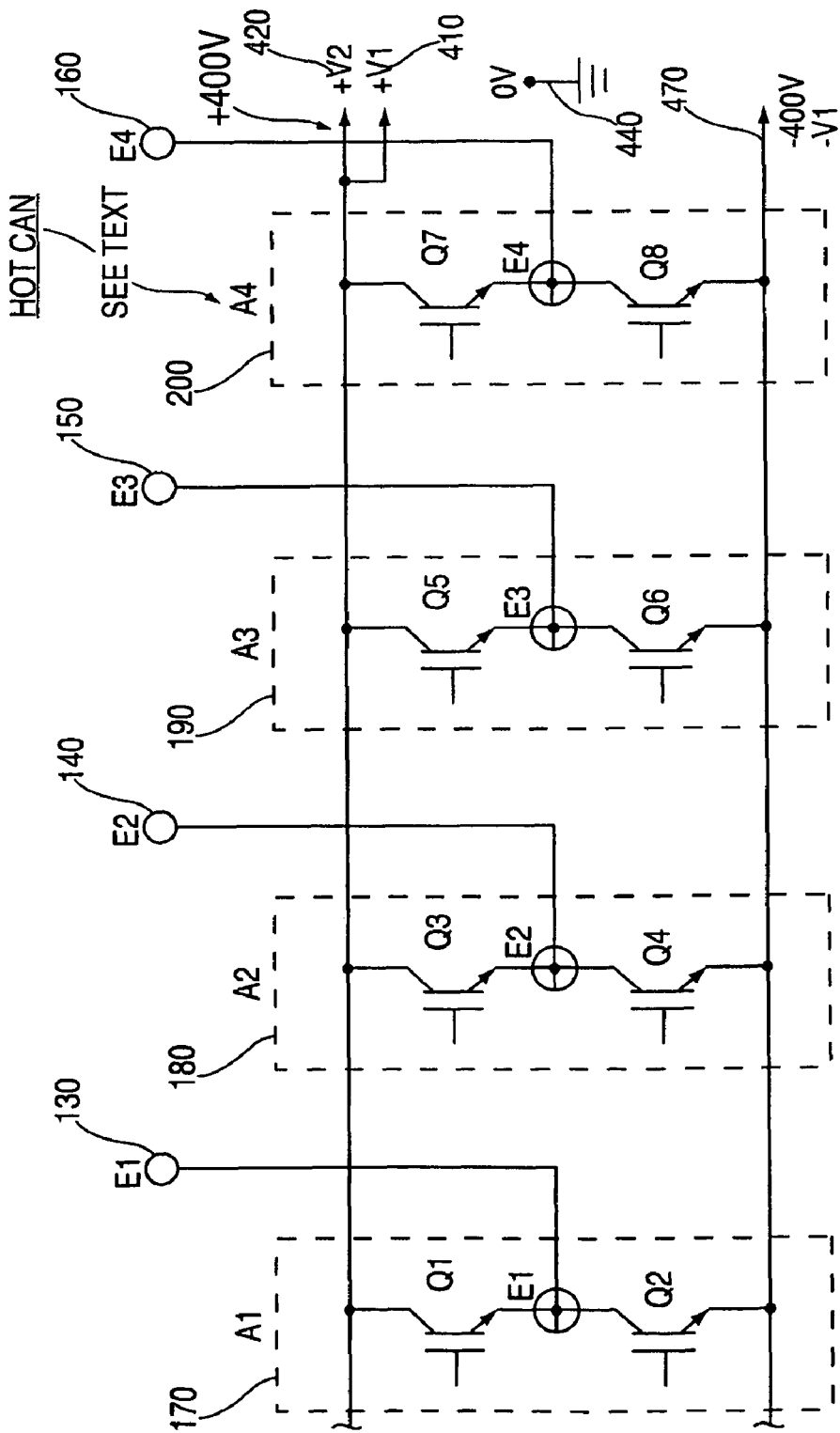
FIG. 2 depicts an amplifier array in which any two, three, or four amplifiers can be driven differentially as to dynamically select current vectors and pathways. Amplifier 4 is assigned to the case for "Hot Can" shocking modes of operation.

FIG. 2 illustrates an amplifier array which is made up of four individual amplifiers A1-170, A2-180, A3-190, and A4-200 with a limited DC bandwidth of 0 to 500 Hz. The bandwidth is designed to deliver rapid defibrillation pulses yet be immune to high frequency noise or interference with other electronic devices. A ground return 440 is shown which represents zero volts. Each amplifier can be differentially driven as in a bridge configuration for current vector selection. IGBT's are depicted as amplifier output power devices; however, MOSFETS, bipolar or other semiconductors or transistor devices may be employed as well to meet the design criteria for the present invention by those skilled in the art of power electronics design. Amplifier 4 is assigned as an electrode when the "Hot Can" shocking mode is selected. Power supply voltages of +400V 420 and −400V 470 are available for each half cycle of the shocking waveform which represents 0 to 800V peak to peak for positive and negative shock pulses. This system dynamically steers or selects different current vectors and different angular delivery perspectives sequentially or simultaneously as to reduce the total energy requirements for ventricular defibrillation and to terminate ventricular tachycardia.

Figure 3:
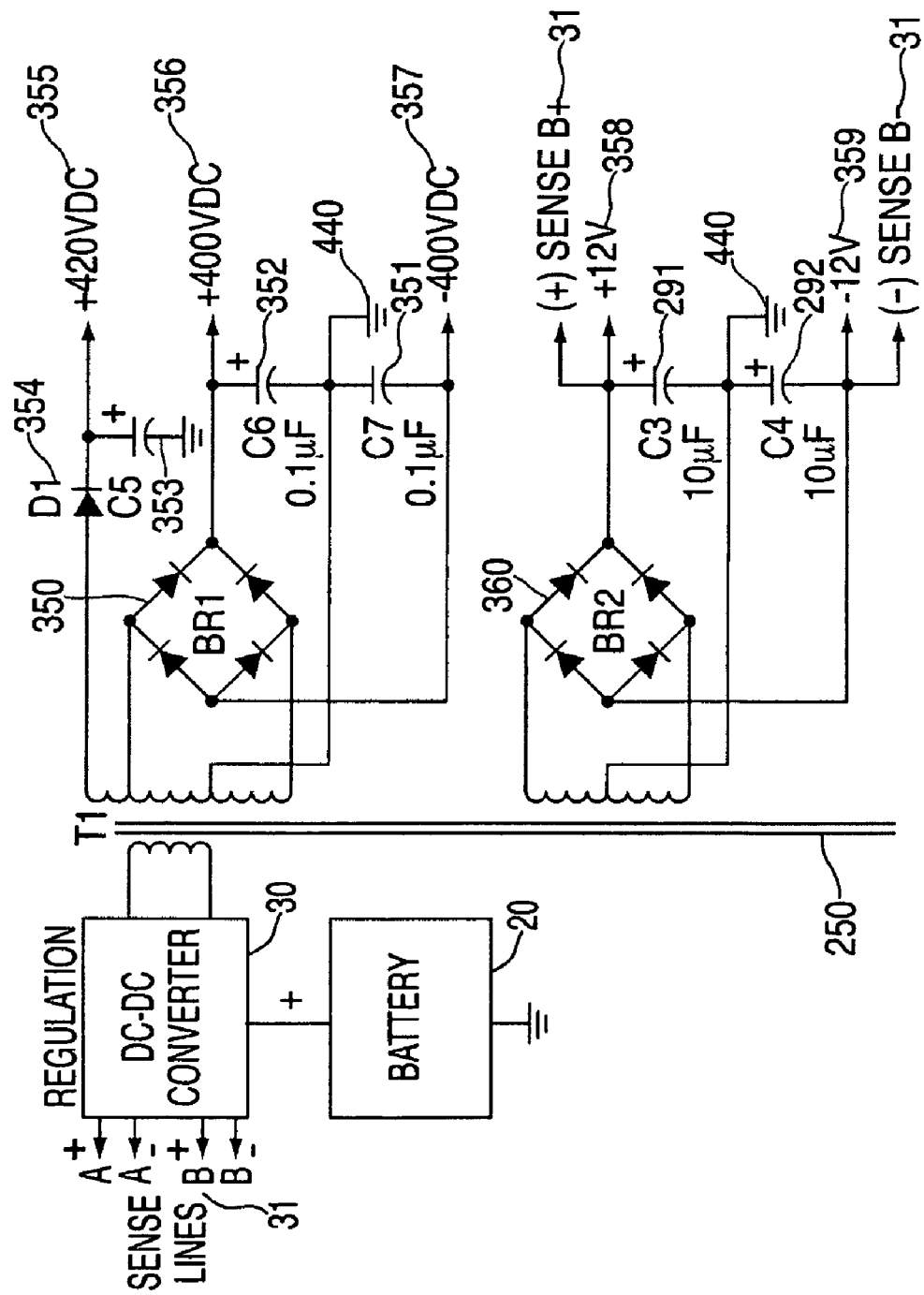
FIGS. 3 and 3A depict the DC/DC converter associated with its secondary power supplies for delivery of low voltage to control circuits and high voltage to the amplifier array. The high voltage capacitor charging circuit is depicted in FIG. 3A.
Figure 3A:
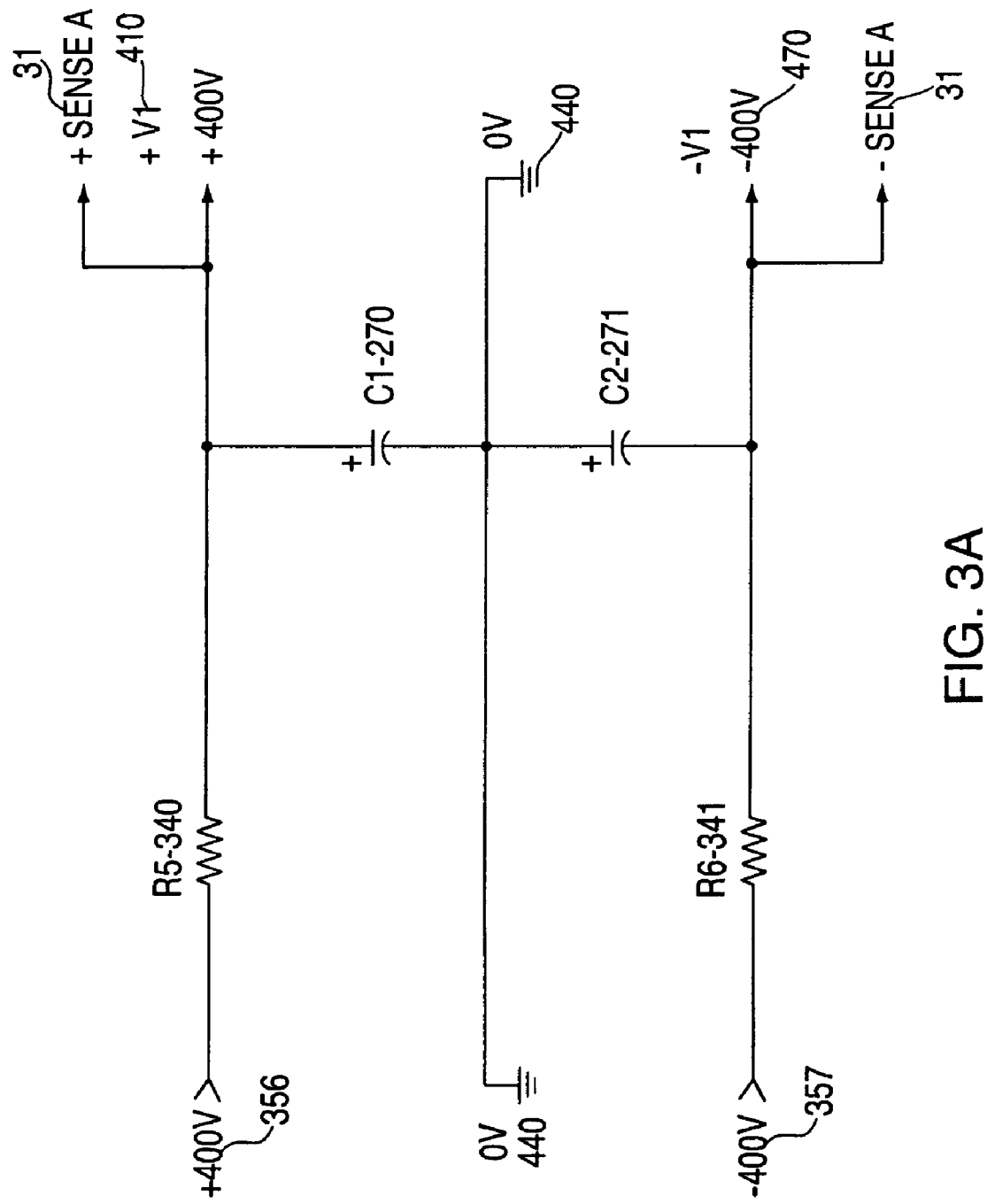

FIGS. 3 and 3A illustrate the design architecture for the power supplies used in the present invention. A PWM regulated DC/DC converter 30 is powered by the battery 20 which converts a low voltage from the battery 20 to a higher voltage output via switching circuitry within the DC/DC converter 30 and is delivered through the transformer T1-250 for isolation from primary to secondary. Voltage regulation is achieved via the sense 31 or feedback lines. T1-250 delivers voltage and current to BR2-360 which convert the alternating current and voltage from T1-250 into a DC voltage and current which is then filtered using C3-291 and C4-292 and delivered to the control electronics in FIG. 1 as +12 VDC-358 and −12 VDC-359. T1-250, D1-354, and C5-353 comprise a separate transformer winding along with rectification and filtering for the purpose of supplying a high side driver voltage 355 set at +420V for the IGBT power devices. In a similar fashion BR1-350 and filter capacitors C6-352 and C7-351 deliver high DC voltages and current to the amplifier rails A1-170, A2-180, A3-190, and A4-200. A ground return 440 is shown which represents zero volts. R5-340, C1-270 and R6-341, C2-271 form capacitor charging circuits which charge over a brief time period of approximately 6-10 seconds prior to the sequential or simultaneous pulse deliveries. C1-270, C2-271 are discharged onto the high voltage rails during the selected shocking protocols. The value of C1-270 and C2-271 will be approximately 100 uF-300 uF rated at 500 WVDC. C1-270 and C2-271 through R5-340 and R6-341 are charged to a high voltage of +/−400 VDC via T=RC×5 time constants to achieve a 99% voltage charge. D2-325 rectifier diode is in series with the high voltage output of the converter 30 for the purpose of gating the voltage and current so as to not interfere with the capacitor discharge circuit and supplies a high side drive voltage for the upper IGBT. Any combination of biphasic waveform pulses and amplitudes may be selected and programmed such as a positive pulse being an exponential ascending waveform and the negative waveform may be programmed to be a square wave or a truncated exponential waveform with descending tilt that comprises a biphasic pulse.

Figure 4A:
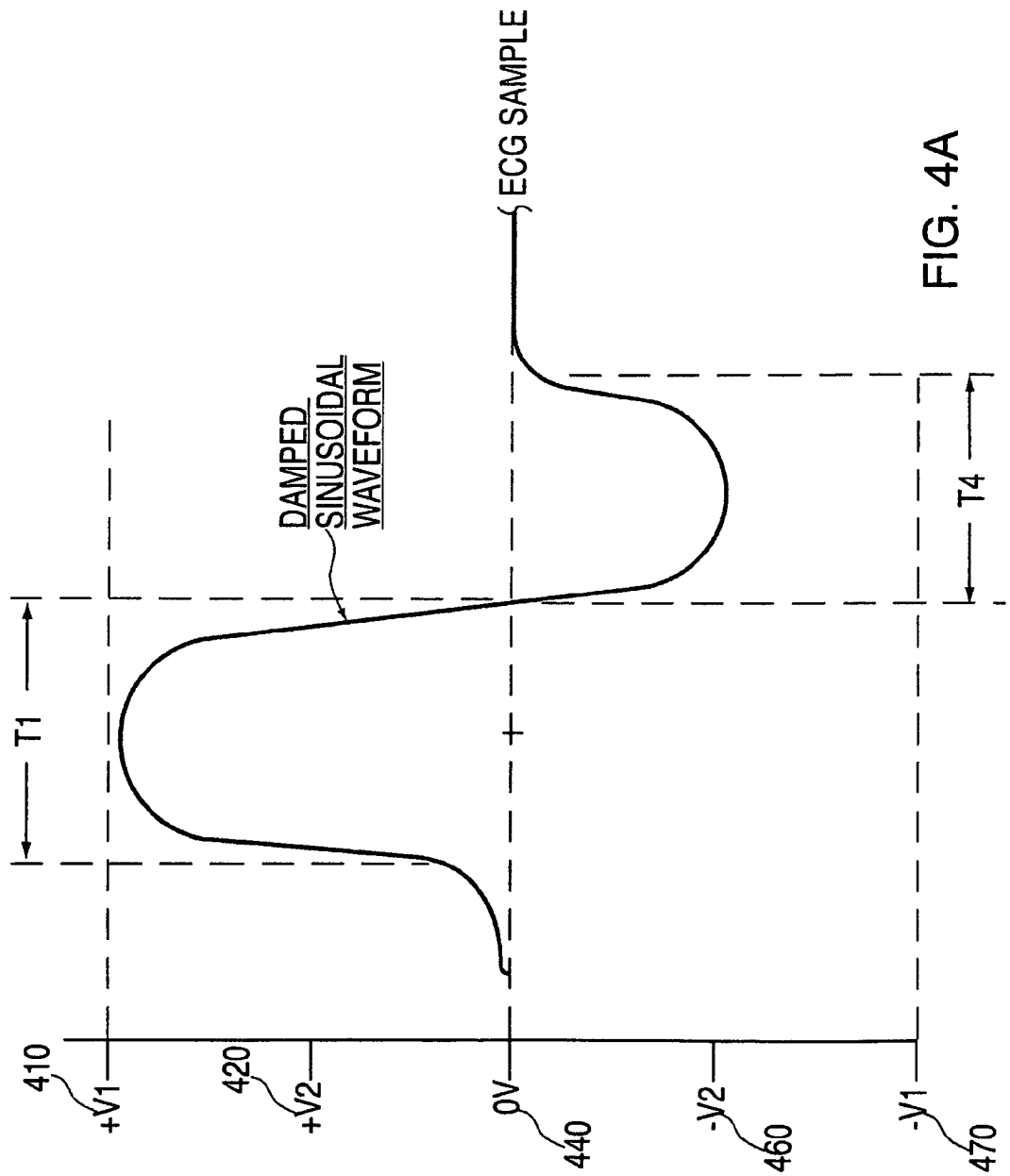

FIGS. 4 and 4A illustrate exemplary ascending and descending exponential, ramp, and damped sinusoidal ramp waveforms with timing and amplitude points of interest. Positive voltage levels of interest are depicted as +V1-410, +V2-420, and +V3-430 as well as negative voltage levels −V1-470, −V2-460, and −V3-450. The positive or negative V3 voltage threshold may be started at any value from zero to 100 volts with 25-75 volts being the most efficient starting point for a shock. Starting V3 at zero wastes time and energy especially for the ascending exponential, ramp, or damped sinusoidal waveforms. The 0V ground return 440 is at a zero state and is a reference for the other voltage potentials. Time periods T1-370 and T4-400 represent the total time duration of the positive and negative pulse durations. ECG sense amp and analyze 60 and 70 occur between defibrillation shock intervals to check the progress of the ventricular fibrillation or ventricular tachycardia conversion. The DC/DC converter runs to charge the shocking capacitors C1-270 and C2-271. The high voltage and currents are delivered by the shocking capacitors C1-270 and C2-271 through the amplifier array.

Figure 5:
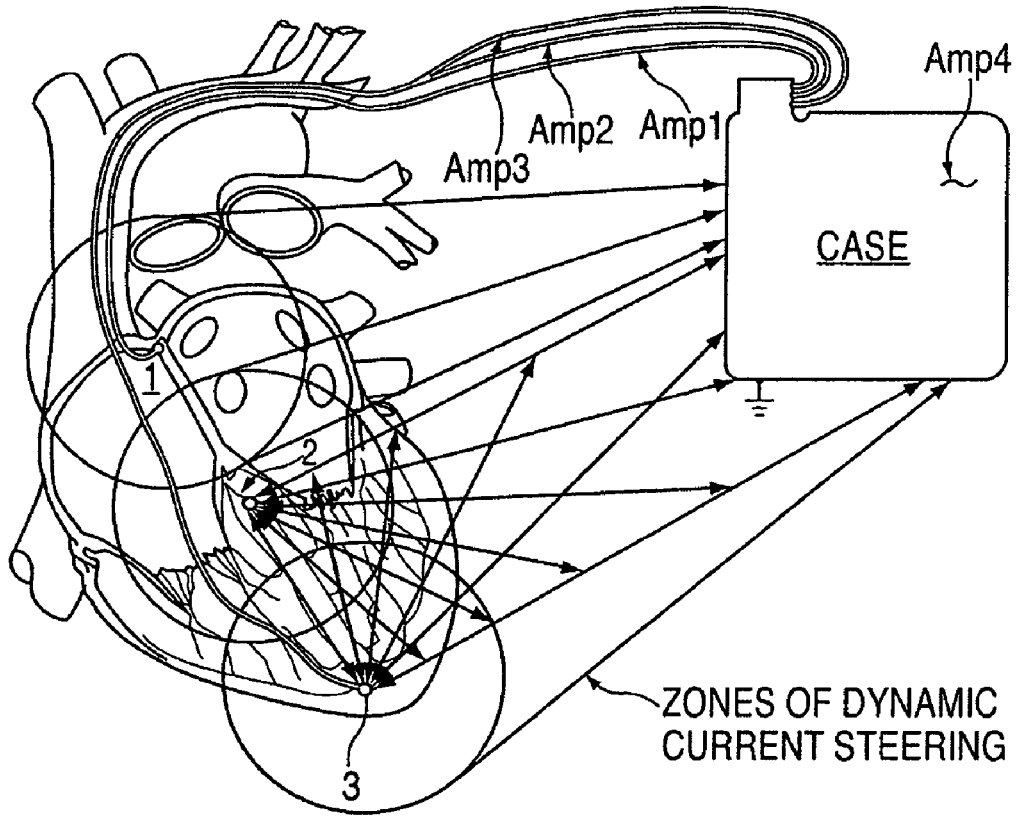
FIG. 5 depicts the right and left ventricles of the heart where an electrophysiologist will select and install electrodes that are placed chronically in the right atria and right ventricle. These structures are entered from the superior vena cava [SVC].

FIG. 5 illustrates possible wire and electrode placement and locations that an electrophysiologist cardiologist skilled in the art of arrhythmia management may choose for successful defibrillation or cardioversion using sequential or simultaneous shocks for VF and or VT. Zones of dynamic current steering with electrode configurations are depicted. By applying different voltage amplitudes, pulse widths, and pulse shapes through the heart muscle via the electrodes provided, sequentially or simultaneously, the voltage and current may be dynamically steered to achieve the desired results for defibrillation or cardioversion.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A method of treating ventricular fibrillation or ventricular tachycardia in a patient, which comprises sequentially or simultaneously delivering to the patient's heart through at least two leads or electrodes signals having arbitrary waveforms for defibrillation, wherein the amplitude of voltage and/or current for each lead or electrode is varied by using an amplifier array to change the transmembrane potential in the left and right ventricles in the patient's heart sufficiently to halt VF or VT.

2. The method of claim 1, wherein the amplifier array delivers biphasic arbitrary waveform defibrillation shocks across one or more current pathways through the patient's heart.

3. The method of claim 1, wherein an internal or external defibrillator is used.

4. The method of claim 3, wherein an implantable or external defibrillator is used by employing an electronic circuit which uses arbitrary waveforms which consume less energy than conventional defibrillation devices thereby reducing pain levels, tissue stunning, and damage associated with very high voltage electrical shocks.

5. The method of claim 3, wherein the implantable defibrillator is an ICD.

6. The method of claim 1 which can treat VT of any mechanism, whether occurring in the structurally normal heart, hypertrophic heart, or myopathic heart.

7. The method of claim 6, wherein the VT is automatic, triggered, or reentrant or VF.

8. The method of claim 1 which is accomplished by using unique arbitrary waveform shocks rather than traditional devices which defibrillate through a single current path.

9. A method of treating ventricular fibrillation or ventricular tachycardia in a patient, which comprises delivering biphasic ascending exponential, ramp, or damped sinusoidal waveforms which are compatible with the transmembrane potential response within the myocardium by using an amplifier array where any two, three, or four amplifiers and their respective electrodes may be driven differentially to draw current through selected current pathways or different angular perspectives within the right and left ventricles to rapidly terminate VF or VT.

10. The method of claim 9, wherein unique electrical shock techniques are employed to match the transmembrane potentials and RC time constants within the myocardium using specialized electronic power amplifier designs and software commands to deliver arbitrary waveform defibrillation and cardioversion shocking pulses through the myocardium.

11. The method of claim 9, wherein any one amplifier may be driven differentially to any of the other amplifiers simultaneously using the same arbitrary waveform or any one amplifier may be driven differentially to any of the other amplifiers sequentially using individual arbitrary waveforms at different or equal voltage and current amplitudes.

12. The method of claim 11 which comprises "Hot Can" shocking or intracardiac electrode shocking as specified or programmed by an electrophysiologist.

13. The method of claim 12, wherein the electrophysiologist can select pre-programmed and pre-defined software waveform protocols, wherein many combinations of shock deliveries are possible based on individual patient requirements for cardioversion or defibrillation.

14. The method of claim 13, wherein combinations of defibrillation or cardioversion shocks are available for selection and delivered via a single shock protocol using arbitrary waveforms.

15. The method of claim 13, wherein the individual requirements are selected from the software protocol based on various medical criteria as defined by the electrophysiologist.

16. The method of claim 9, wherein waveform protocols are pre-programmed and pre-defined and are loaded into a microcontroller memory for quick execution.

17. The method of claim 16, wherein 50 to 100 or more protocols can be stored in the microcontroller for an electrophysiologist to select from.

18. The method of claim 9, wherein arbitrary waveforms can be delivered to multiple electrode configurations and multiple sequential or simultaneous shocking paths can be employed.

19. The method of claim 9, wherein the amplifiers will process any voltage and/or current arbitrary waveform geometry through the ventricles and or atria as directed by an electrophysiologist.

20. The method of claim 19, wherein the waveform is ascending or descending exponential, ramp, damped sine, square, sine, triangle, or saw tooth.

21. A method of treating ventricular fibrillation or ventricular tachycardia in a patient which comprises providing an implantable or external ventricular defibrillation and or ventricular tachycardia cardioversion device which uses less energy than conventional defibrillation devices thereby reducing pain levels, tissue stunning, and damage associated with very high voltage electrical shocks, wherein transmembrane potentials are achieved using sequential or simultaneous arbitrary waveform shocks.

22. The method of claim 21, wherein biphasic sequential or simultaneous shocking pulses are in the range of from about 2.5 ms to about 8 ms positive and negative time periods, respectively, to minimize energy consumption and conserve battery life.

23. An apparatus for treating ventricular fibrillation or ventricular tachycardia, which comprises
means for sequentially or simultaneously delivering to the patient's heart through at least two leads or electrodes signals having arbitrary waveforms for defibrillation; and
an amplifier array,
wherein the amplitude of voltage and/or current for each lead or electrode is varied by using the amplifier array to change the transmembrane potential in the left and right ventricles in the patient's heart sufficiently to halt VF or VT.

24. The apparatus of claim 23, wherein the amplifier array delivers biphasic arbitrary waveform defibrillation shocks across one or more current pathways through the patient's heart.

25. The apparatus of claim 23 which comprises an internal or external defibrillator.

26. The apparatus of claim 23 which can treat VT of any mechanism, whether occurring in the structurally normal heart, hypertrophic heart, or myopathic heart.

27. An apparatus for treating ventricular fibrillation or ventricular tachycardia in a patient, which comprises means for delivering biphasic ascending or descending exponential, ramp, or damped sinusoidal waveforms which are compatible with the transmembrane potential response within the myocardium by using an amplifier array where any two, three, or four amplifiers and their respective electrodes may be driven differentially to draw current through selected current pathways or different angular perspectives within the right and left ventricles to rapidly terminate VF or VT.

28. The apparatus of claim 27, wherein any one amplifier may be driven differentially to any of the other amplifiers simultaneously using the same arbitrary waveform or any one amplifier may be driven differentially to any of the other amplifiers sequentially using individual arbitrary waveforms at different or equal voltage and current amplitudes.

* * * * *